United States Patent
Paplow et al.

(10) Patent No.: US 6,588,444 B2
(45) Date of Patent: Jul. 8, 2003

(54) THERAPEUTIC GAS TUBE SAFETY REEL HAVING EASY TUBE REPLACEMENT MEANS AND METHOD OF REPLACEMENT

(75) Inventors: Adam Paplow, Castlerock, CO (US); Scott Nathanson, Englewood, CO (US); Lynn M. Taussig, Greenwood Village, CO (US)

(73) Assignee: Medical Safety Devices, LLC, Castlerock, CO (US)

( * ) Notice: Subject to any disclaimer, the term of this patent is extended or adjusted under 35 U.S.C. 154(b) by 0 days.

(21) Appl. No.: 09/887,782

(22) Filed: Jun. 22, 2001

(65) Prior Publication Data

US 2002/0195143 A1 Dec. 26, 2002

(51) Int. Cl.$^7$ ................................................ B65H 75/34
(52) U.S. Cl. ............................ 137/15.01; 137/355.26; 137/551; 137/355.23; 242/385
(58) Field of Search ................ 137/355.26, 355.16, 137/355.23, 15.01, 551, 559; 242/385

(56) References Cited

U.S. PATENT DOCUMENTS

| | | | | |
|---|---|---|---|---|
| 2,742,242 A | * | 4/1956 | Godwin | 242/89 |
| 3,457,946 A | * | 7/1969 | Dean, Jr. et al. | 137/355.26 |
| 4,227,661 A | * | 10/1980 | King et al. | 242/385.2 |
| 4,384,688 A | * | 5/1983 | Smith | 242/378.2 |
| 4,543,982 A | | 10/1985 | Wolfe | 137/355.2 |
| 4,713,059 A | * | 12/1987 | Bickelhaupt et al. | 604/171 |
| 4,713,497 A | | 12/1987 | Smith | 191/12.2 |
| 5,094,396 A | | 3/1992 | Burke | 242/107.1 |
| 5,392,808 A | | 2/1995 | Pierce | 137/355.23 |
| 5,560,391 A | * | 10/1996 | Bantaculo | 137/355.23 |
| 5,826,608 A | | 10/1998 | Pierce | 137/15 |
| 5,893,528 A | | 4/1999 | Strokosz et al. | 242/373 |
| 5,975,120 A | | 11/1999 | Novosel | 137/355.23 |
| 6,065,490 A | | 5/2000 | Falcone, Jr. | 137/355.23 |

* cited by examiner

*Primary Examiner*—A. Michael Chambers
(74) *Attorney, Agent, or Firm*—Welsh & Katz, Ltd.

(57) ABSTRACT

A safety reel for storing, paying out and rewinding tube is provided. As tubing is paid out of the reel a coil spring is wound tight to provide the energy to recoil the tubing when desired. In this way tubing may be reeled up to a desired length and is thereby not underfoot, causing potential tripping hazards and tube crushing situations. The safety reel of the present invention allows the quick and easy replacement of tubing. The reel and case are provided with easy alignment devices such that the internal reel hose guide inlet and the external case payout opening may be quickly and easily aligned together so that tubing may be quickly and easily replaced. In this manner the user is encouraged to replace the tubing at recommended intervals so that germs, bacteria and the like are minimized and the user's health is better protected. In a preferred embodiment the removal and replacement of tubing is facilitated by providing a manipulatable knob with precise indicia to assist in aligning the reel and casing for quick removal and replacement.

29 Claims, 8 Drawing Sheets

THERAPEUTIC GAS TUBE SAFETY REEL HAVING EASY TUBE REPLACEMENT MEANS AND METHOD OF REPLACEMENT

FIELD OF THE INVENTION

The present invention concerns a novel gas supply reel that allows persons using therapeutic gas to easily coil in or pay out an amount of tubing to allow the person to be in any part of a room without having extra tubing underfoot. More specifically, the present invention concerns a therapeutic gas reel that includes a quick alignment mechanism and a method of tube replacement, which allows the easy removal of used or otherwise contaminated tubing and complete replacement with fresh tubing.

BACKGROUND OF THE INVENTION

The use of oxygen or other therapeutic and anesthetic gases in hospitals, clinics, at home, and in other medical situations often requires an individual's connection to a fixed source of the gas. Typically, the source of the gas and the location of the patient, for therapy, surgery, rest or other procedure, changes depending on the time of day, procedure or location of equipment. As a result, patients can rarely be provided with a length of tubing that will exactly accommodate the patient's needs at all times. Typically, the patient is given a large amount of tubing such that the patient may travel or be moved to all corners of a therapy room without running out of tubing.

In hospitals, oxygen and other therapeutic gases are typically provided through built in sources found as wall outlets. At clinics, doctor's offices, and homes, therapeutic gases are typically provided in heavy compressed gas canisters that, while more portable, are often quite heavy (and not conducive for movement, particularly by infirm individuals, and because of the potential explosive nature of gases under pressure). As such, gas sources are usually fixed in place in a therapy room and lengths of tubing are provided between the source and the user. This has often resulted in long lengths of such tubing being laid such that it is underfoot both for the person using the therapeutic gas line and for those visiting or providing therapy. Such tubing can become a safety hazard to the user of the tubing and to those visiting or working near and around the user. The tubing can get trampled by feet or equipment, causing kinking, crushing or tearing of the tubing and providing a risk of severing the user from the supply of gas, or allowing the introduction of bacteria, germs or other contaminants into the gas line. Further, tubing underfoot can cause a tripping or entanglement hazard to the user and others in the vicinity.

To alleviate this problem some users of therapeutic gases will collect and wind, or reel, the excess tubing and lay it aside. This, however, provides the added complication of forming an entanglement and potentially also forming a kink in the tubing, requiring the user to untangle the tubing when movement is desired, or to find the kink when it is discovered that therapeutic gas has been limited or cut-off by a kink in the tubing. Reels, resembling garden hose reel devices, onto which a length of tubing may be placed and payed-out or reeled-in as needed, have begun to appear. These devices have generally been undesirable in that they do not allow for the easy and/or rapid removal and replacement of tubing. In such units, replacement of tubing, typically, can be so difficult as to discourage the user from regularly replacing the tubing. As a result, users, who can only stand a short time off of their supply of gas, and the elderly, or persons having physical handicaps may not change the gas supply tubing often enough to insure a healthy and sanitary carrier for oxygen or other gases. Further, some of these reels include built in, non-interchangeable, connection parts which may, after some use, cause the collection of germs, bacteria or other contaminants to be transferred from the reel to the tubing and the patient in due course.

We have invented a new and novel therapeutic gas tube reel that provides a means to supply gas to a user while keeping a significant length of reserve tubing stored until needed in a convenient container. The tubing is reeled into the device such that the flow of gas is continuous through the stored tubing and to the patient. The device of our invention allows the quick and easy alignment of an inner reel and an outer casing such that the tubing may be quickly and easily exchanged as needed. Further the device provides a swivel hub which allows the rotation of the device without kinking the tubing within. Further, the swivel device is changeable, being typically connected only to the supply of therapeutic gas, through a tube, and to the tubing in the invention. The tubing and swivel device is otherwise unconnected to the reel or case. The present invention further comprises means to retract the tubing, which has been paid out, back into the reel when a smaller length of tubing is desired.

It is therefore an object of the present invention to have a device that would allow for the storage of a length of clean and sanitary gas tubing, and allows the easy pay out and collection of the gas tubing. It is a further object of the present invention to have a reel device that is spring loaded to assist in the reeling of tubing which has been payed out. It is a further object of the present invention to have a reel device in which sterile elements are only contacted by parts which can also be easily removed and sterilized or replaced. It is a further object of the present invention to have an easy and rapid means of removing and replacing the entire length of gas tubing, such that removal and replacement can be done often to avoid the problems of bacteria, germs and other contaminants.

Other objects and advantages of the present invention will become apparent as the description proceeds.

SUMMARY OF THE INVENTION

In accordance with the present invention, a safety reel for therapeutic gas tubing, comprising: a case defining a tube opening and a reel alignment means is provided. A reel for storing tubing is also provided, the reel comprising a case alignment means, a barrel having a tube inlet defined therethrough and a hub and a tube passageway defined between the opening and the hub. In one embodiment of the device a spring, attached to the reel and the case, is provided such that the payout of tubing causes the spring to coil so that the tubing may be recoiled into the case and onto the reel when desired. In a further embodiment, the spring retraction governed by a ratchet such that recoil tension on the tubing can be controlled as desired. The safety reel further comprises an air swivel for connecting the air tubing to a source of therapeutic gas such that the tubing is not twisted when it is wound up onto the reel.

In one embodiment the alignment means, of the real and case, are automatically controlled such that the movement of a knob towards an alignment indicator causes the alignment of the reel and case to facilitate the complete replacement of the tubing.

In a preferred embodiment, the reel and case are made of a strong and durable plastic material, allowing for a lightweight and low cost device having considerable structural strength and integrity.

In a further embodiment, the length of tubing, within the reel, is connected solely to a replaceable device that is itself connected solely to the gas supply source. In a preferred embodiment the connection is by means of a swivel device that allows connection of tubing to a supply line while allowing the tubing to be coiled and paid out without entanglement of the line. The swivel device is designed to be disposable such that it may be removed and disposed of, and a new swivel device attached when fresh tubing is installed.

In a further embodiment, the safety real includes a swivel bracket for mounting the assembly to wall or oxygen source such that the reel and housing tracks the user as they move about.

Further, a method of installing and easily replacing tubing is provided in the present invention. The method includes the steps of providing a storage case that comprises a tube inlet, for inserting and paying-out tubing, and a reel alignment indicator. The method, further, includes the steps of providing a length of tubing, of the type used with therapeutic gases, and providing a tube reel on which to hold the tubing. The provided reel comprises a case alignment means and a barrel portion defining a tube opening. The reel further defines a hub and a tube passage, between the tube opening on the barrel and the hub. The hub defines an exterior opening of the tube passage and is the situs for bringing therapeutic gases into the case.

The method further includes aligning the case tube inlet and the barrel tube opening by manipulating the reel and aligning the reel alignment opening with the case alignment opening respectively on the case. Further, the method includes, inserting the tubing into the aligned case tube inlet and the reel tube opening, manipulating the length of tubing through the tube passage and to the hub for connection to tubing swivel and then to an external source of therapeutic gas.

In a preferred embodiment, the method is improved by providing a reel alignment indicator, on the case, that shows when the reel is aligned for replacement of the tubing. In the method of the present embodiment, the case tube inlet and the barrel tube opening may be aligned with each other by manipulating the reel and aligning the reel alignment indicator.

In replacing therapeutic gas tubing presently within a safety reel of the present invention, the inventive method includes the steps of paying out substantially all tubing within the case, aligning the case tube inlet and the barrel tube opening by manipulating the reel and aligning the reel aligning opening and the case aligning opening, respectively on the case and reel and pulling the tubing from the device. The user then provides a new length of tubing, which is installed according to the method described above. In a preferred embodiment, the tubing swivel is replaced when the tubing is replaced.

A more detailed explanation of the invention is provided in the following description and claims and is illustrated in the accompanying drawings.

DETAILED DESCRIPTION OF THE ILLUSTRATIVE EMBODIMENT

Figure 1:
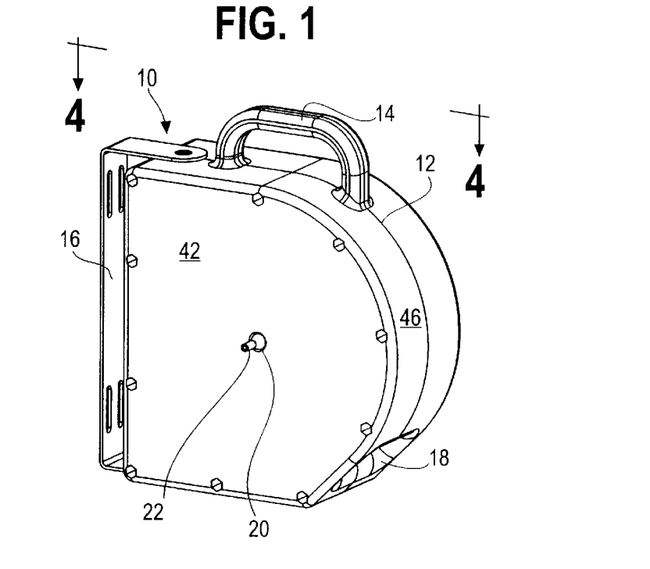
FIG. 1 is a perspective view of an therapeutic gas reel of the present invention.
Figure 2:
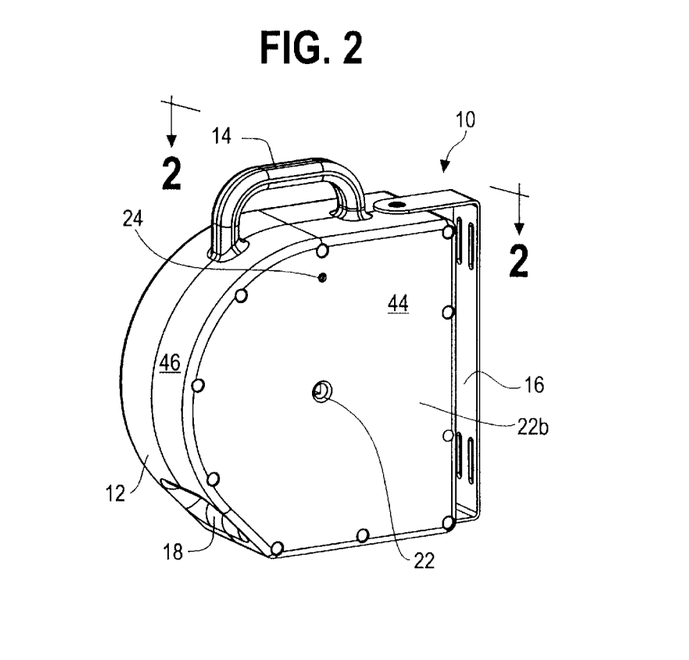
FIG. 2 is a perspective view, from another angle, of the reel of FIG. 1.

Referring to the drawings, a therapeutic gas safety reel 10 is shown having a case 12 a handle 14, a wall mount 16. Safety reel 10 further comprises a tube inlet 18 a hub 20 an air swivel 22, loosely held in hub 20, a manual rewind socket 22 and an alignment opening 24.

Within case 12 safety reel 10 is seen (FIGS. 3 and 4) to comprise a tubing reel 30. Tubing reel 30 comprises a barrel portion 32 held concentrically within two extended plate-like flanges 34, as in a typical reel. The area between barrel portion 32 and the inner walls 34a of flanges 34 comprise a tube storage area 36. Barrel portion 32 defines a hose guide inlet 38 comprising the opening of a tube passage 40 connecting storage area 36 with hub 20.

Figure 5A:
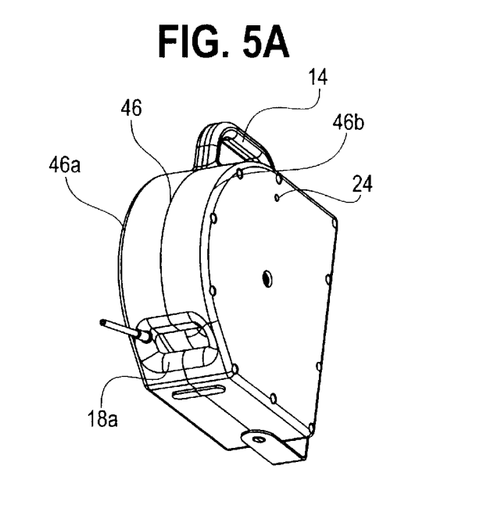
FIG. 5a is a perspective view illustrating steps of the method of the present invention.
Figure 5B:
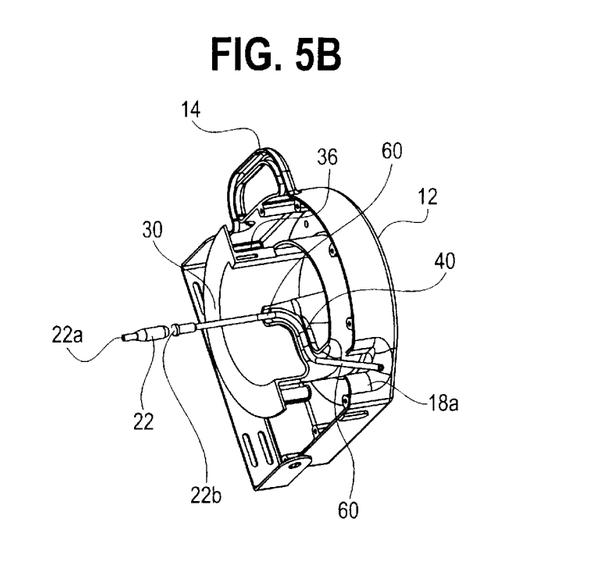
FIG. 5b is a perspective view illustrating steps of the method of the present invention.
Figure 5C:
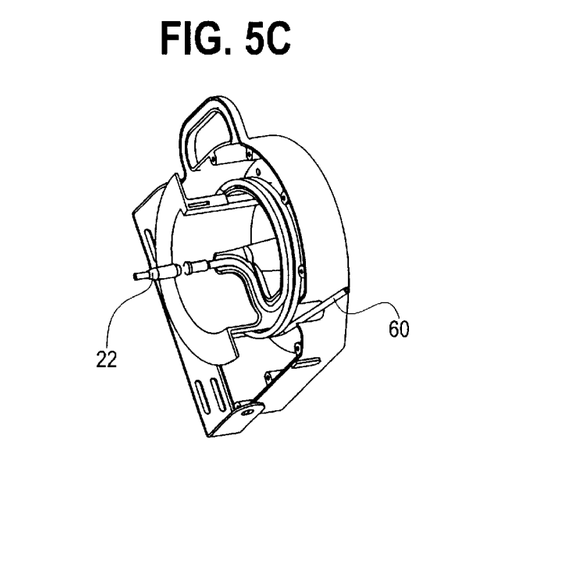
FIG. 5c is a perspective view illustrating steps of the method of the present invention.
Figure 6:
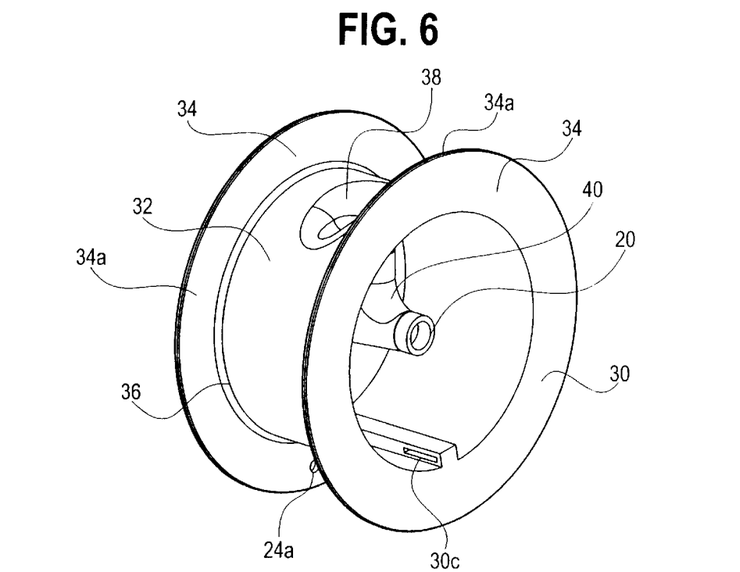
FIG. 6 is a perspective view of a reel used in an embodiment of the present invention.
Figure 7:
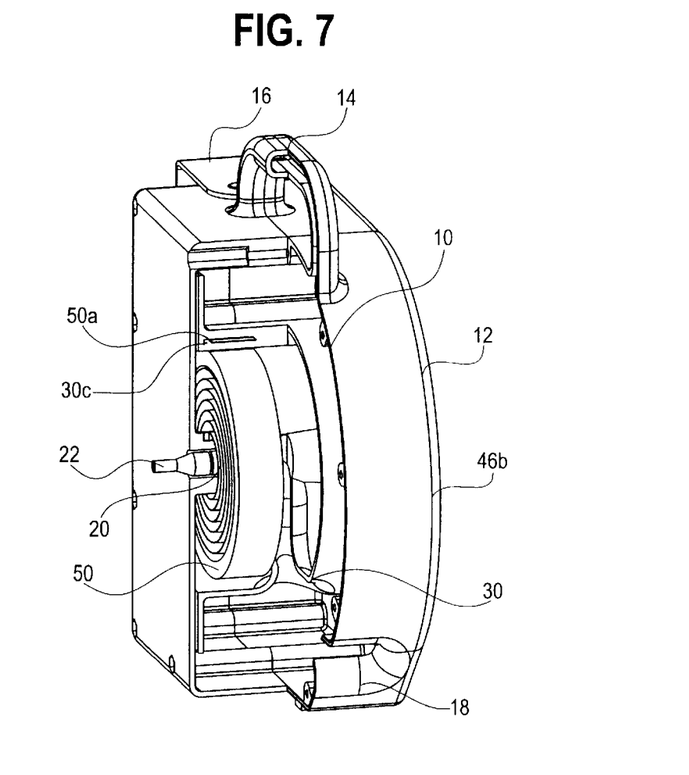
FIG. 7 is a partially cut away perspective view of an embodiment of the present invention.

Case 12 comprises generally two side portions 42 and 44, which are generally perpendicular to each other and a center cover 46. Center cover 46 further defines a tube inlet opening 18. In one embodiment, center portion 46 is divided in two parts 46a and 46b (FIG. 5) which are each attached to one of the two side portions 42 and 44, such that the parts form a clam shell-type case. In this embodiment, a tube inlet piece 18a is provided and is placed into an opening defined in both center portion parts 46a and 46b. Tube inlet opening 18 or tube inlet piece 18a provide a means to pay out and retrieve tubing from reel 30 through case 12. It is to be understood that any manner of comprising, providing or forming an outer shell or case for the inner reel device may be used without departing from the novel scope of the present invention. Further, it is to be understood that the access means (18 or 18a) for the tubing into case 12 may be comprised, or defined, in any manner without departing from the novel scope of the present invention.

Figure 3:
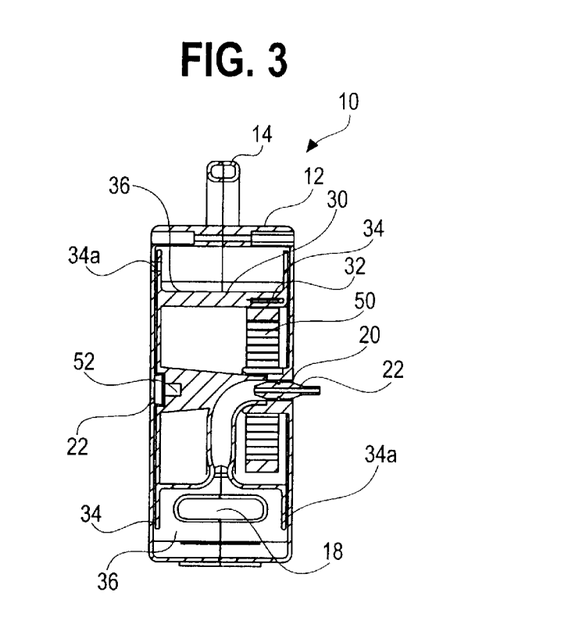
FIG. 3 is a cross-sectional view of the reel of FIG. 2, taken along the plane of line 2—2 of FIG. 2.
Figure 4:
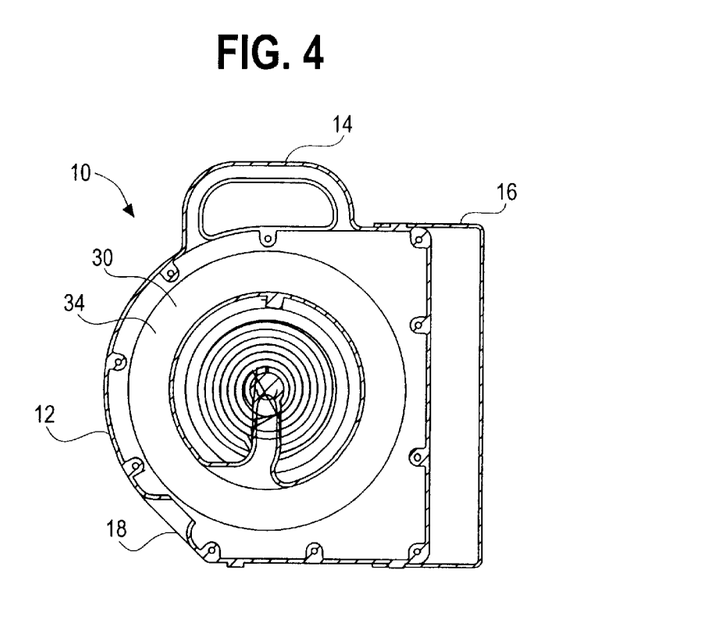
FIG. 4 is a cross-sectional view of the reel of FIG. 1, taken along the plane of line 4—4 of FIG. 1.

As shown in FIGS. 3 and 4, a rewind spring 50 and a recoil spring pre-load ratch drive socket 52 are provided to assist, if needed, in rewinding paid out tubing. It is to be understood that tubing may be rewound into housing 12 by other means, such as a rewind handle, a motor or other means, as known by persons having ordinary skill in the art, with out departing from the novel scope of the present invention. Recoil spring 50 is shown as a coiled metal spring, however, it is to be understood that other types of springs may be utilized without departing from the novel scope of the present invention. As tubing is paid out of case 12, tube reel 30 rotates causing spring 50, which has an end 50a attached to a re-wind spring clip 30c in reel 30, to be wound tight, storing energy for recoiling tubing. A gear or ratchet assembly, not shown, is typically provided to allow spring 50 to be locked into a wound position without inadvertently or prematurely causing the tubing to be rewound. As is known by persons having skill in the art, the user of the device may rapidly pull on tubing 60, as on a typical pull-down blind, to release the gear or ratchet assembly allowing tubing 60 to be rewound onto reel 30. Socket 52 is provided to allow a standard ratchet driver (not shown) to be inserted so that the user may manually re-wind spring 50 should spring 50 unwind prematurely and/or lose the rewind tension (in any manner or as a result of any event) needed to pull the tubing back onto tubing reel 30.

In the present invention, case 12, tubing reel 30 and spring 50 are assembled together as shown. An air swivel 22 is placed into hub 20, and connected, at a first end 22a, to a source of therapeutic gas, such as a hospital oxygen supply or a compressed canister of therapeutic gas. As can be seen, no direct connection between safety reel 10 and tubing 60 is made. Tubing 60 is connected only to swivel 22. In order to provide a completely aseptic therapeutic gas transfer system, swivel 22 is made such that it is easily attached and removed to safety reel 10, and it is disposable and inexpensively replaced by a new swivel 22 simultaneously with the replacement of tubing 60.

In the placement of tubing, within the device of the present invention, tubing reel 30 is aligned with case 12, using reel alignment opening 24 on case 12 and case alignment opening 24a in reel 30. A supply of tubing 60 is fed into case 12 through inlet 18 (or inlet piece 18a) though reel 30, then through hose guide inlet 38 into tube passage 40. Tube 60 is then further connected to the air swivel other end 22b. Reel 30 is then allowed to recoil (or may be recoiled through socket 52) tubing 60 into case 12. When replacement of tubing 60 is desired, the procedure may be reversed, and new tubing 60 may be attached.

In the use of the safety reel 10 of the present invention, as reel 30 rotates within case 12, in paying out or collecting tubing 60, inlet 18 and inlet 38 are separated along the arc of rotation. In order to effect the removal and replacement of tubing 60, tubing 60 must be paid out to nearly the end of the tubing, inlet 18 must then be aligned with inlet 38. In order to facilitate the alignment of reel 30 with case 12, the user rotates reel 30 until alignment openings 24, on case 12, and 24a on reel 20 are together. When the respective alignment openings are aligned, inlet opening 18 and tube inlet 18a are also aligned. Alignment may be effected easily by placing a thin cylindrical object, such as a pencil or dowel, into opening 24, pushing the thin cylindrical object forward until it drags against reel 30, and paying out or collecting tubing 60 (in any of the manners described herein) until opening 24a is caught on the thin cylindrical object. Reel 30 and case 12 may be held together by the thin cylindrical object, by pushing the thin cylindrical object into case alignment opening 24a, until after tubing 60 is replaced. Withdrawal of the thin cylindrical object then unlocks reel 30 and case 12, allowing reel 30 to rotate freely within case 12.

As tubing 60 is paid out, to the length needed by the user, spring 50 becomes wound and creates potential energy for rewinding tubing 60. When a smaller length of tubing 60 is needed, the user merely pulls sharply on the tubing to cause the ratchet to release from the gears, and tubing to be retracted to the point desired. A further pull on the tubing re-engages the gear and ratchet locking the tubing at the length desired. Further subsequent pulling allows the tube to retracted further, or ultimately to be completely retracted.

Figure 8:
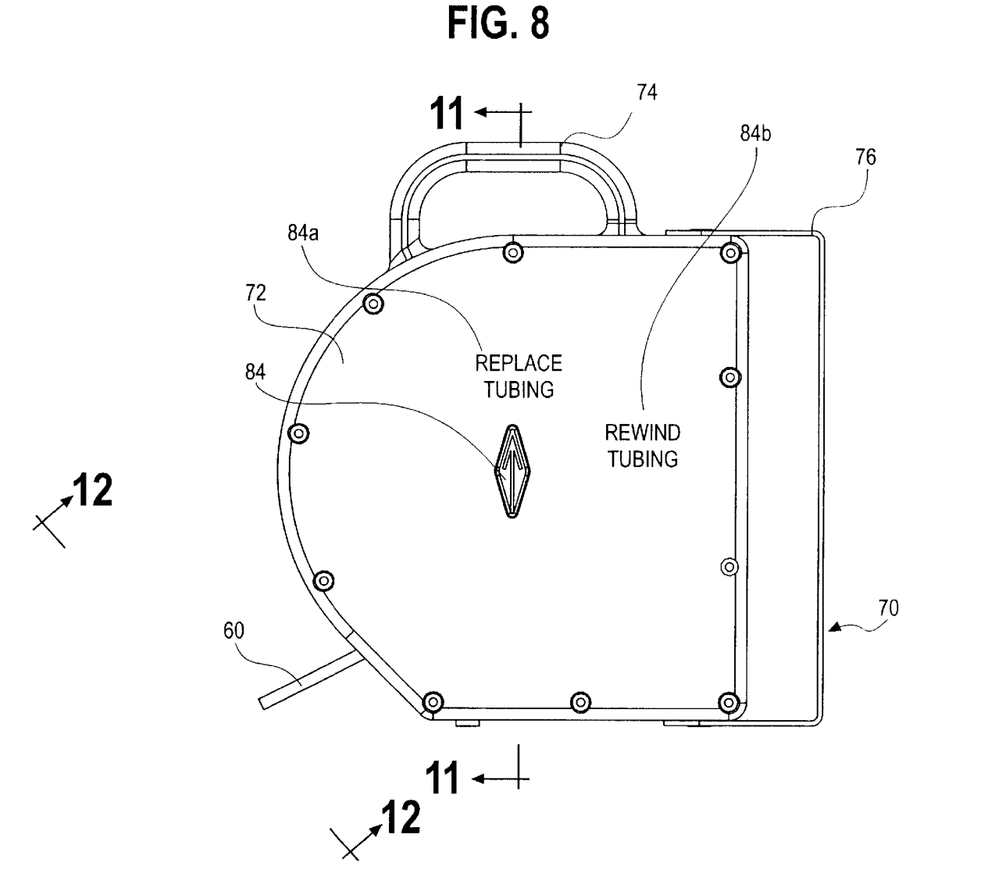
FIG. 8 is a side elevational view of another embodiment of the reel of present invention.

Referring to the drawings, another embodiment of a therapeutic gas safety reel 70 of the present invention is shown having a case 72 a handle 74, a pivoting wall mount bracket 76. Safety reel 70 further comprises a tube inlet 78 a hub 80, an air swivel 82 loosely held in hub 80, an alignment indicator 84 with alignment indication text 84a and 84b.

Within case 72 safety reel 70 is seen (FIGS. 9, 10, 11, and 13) to comprise a tubing reel 86. Tubing reel 86 comprises a barrel portion 88 held concentrically within two extended plate-like flanges 90, as in a typical reel. The area between barrel portion 88 and the flanges 90 comprise a tube storage area 92. Barrel portion 88 defines a hose guide inlet 94 comprising the opening of a tube passage 96 connecting storage area 92 with hub 80.

Figure 9:
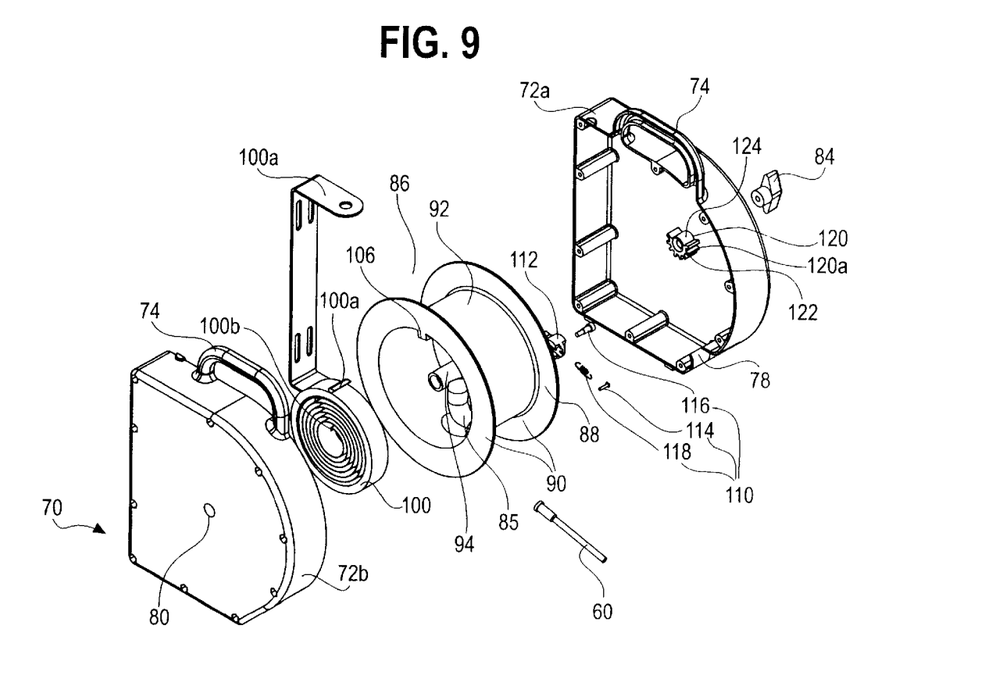
FIG. 9 is an exploded perspective view of the reel of FIG. 8.
Figure 10:
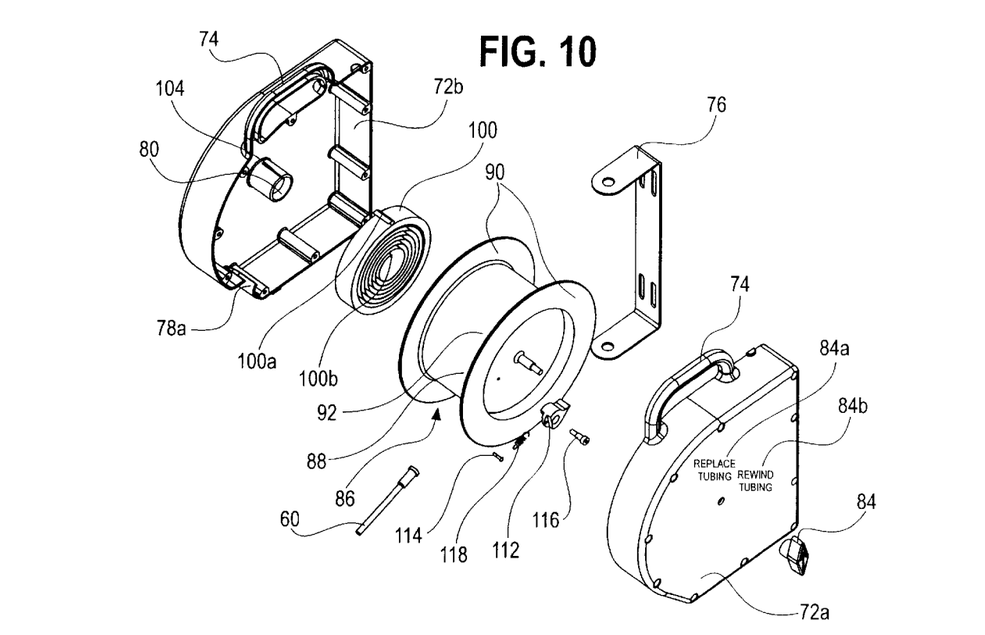
FIG. 10 is an exploded perspective view of the reel of FIG. 8, taken from another angle.
Figure 11:
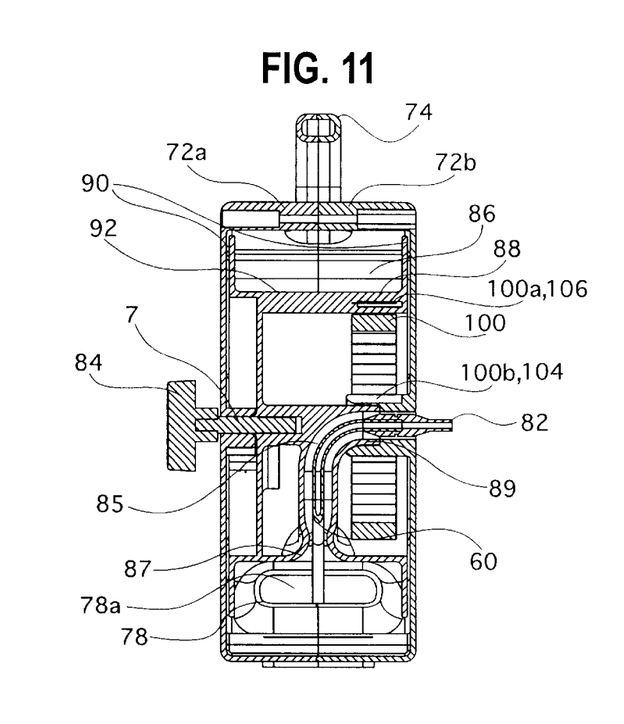
FIG. 11 is a cross sectional view taken along the plane of line A—A of FIG. 8.
Figure 12:
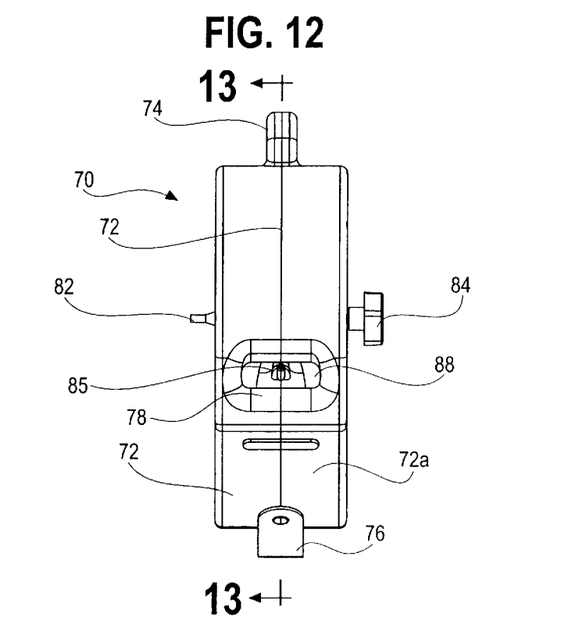
FIG. 12 is an elevational view of the front of a safety reel of FIG. 9 shown without tubing.
Figure 13:
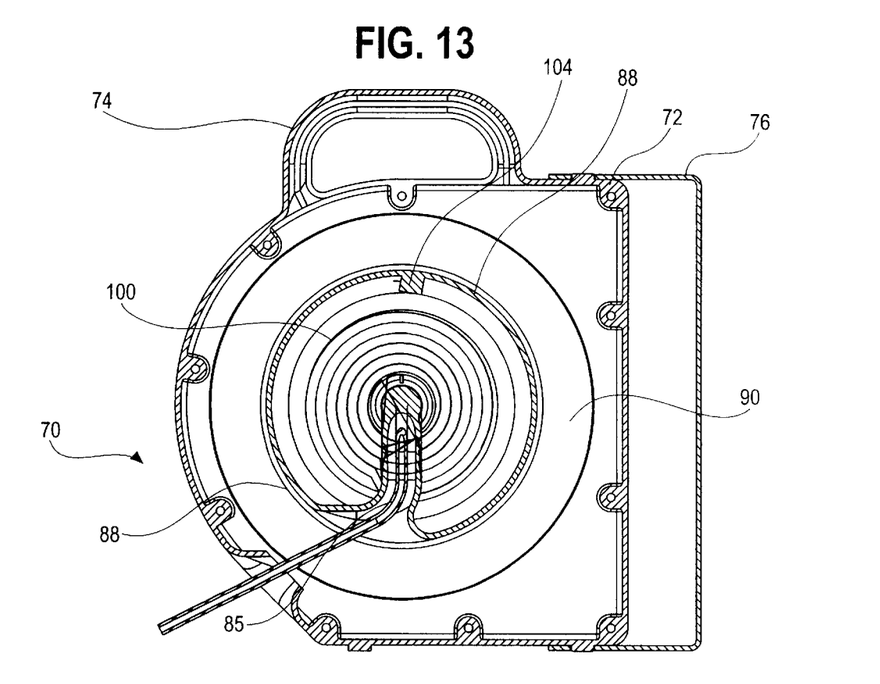
FIG. 13 is a cross sectional view of a safety reel of FIG. 8 taken along the plane of line C—C of FIG. 12.

Case 72 comprises generally two side portions 72a and 72b, which are generally perpendicular to each other and form a tube inlet opening 78a. In one embodiment, a tube inlet path 98 is provided. Tube inlet opening 78a provide a means to pay out and retrieve tubing from reel 86 through case 72. As shown in FIGS. 8, 9, 10, 11, 12, and 13 a rewind spring 100 and reel position indicator 102 are provided to assist in rewinding paid out tubing 60. As tubing 60 is paid out of case 72, tube reel 86 rotates causing spring 100, which has one end 100a attached to a re-wind spring clip 104 in reel 86 and the other end 100b attached to the spring case clip 106, to be wound tight such that energy for recoiling tubing 60 is stored in spring 100. A ratchet assembly 110 (as shown in FIGS. 9 and 10) is provided to allow spring 100 to be locked into a first wound position without inadvertently or prematurely causing the tubing 60 to be prematurely rewound. Ratchet assembly 110 is comprised of a paw 112, a spring post 114, a paw post 116, a ratchet spring 118, having a first end 118a and a second end 118b, a gear 120, having a first segment 120a, having a plurality of gear teeth 122, and a second segment 124, having no gear teeth. In the operation of ratchet assembly 110, the ratcheting action is caused when paw 112 engages the gear teeth 124 of gear 120. As paw 112, which is attached to reel 86 rotates with reel 86, the ratchet spring 118 maintains engagement, at first end 118a, preventing reverse rotation of the reel 86.

As illustrated, second end 118b of ratchet spring 118 is constrained by spring post 114, which is also affixed to reel 86. When paw 112 rotates past the first segment 120a of gear 120 to the toothless second segment 120b, paw 112, can be disengaged by reverse rotation of the reel 86. It is to be understood that alternative means of controlling spring118, other than by use of the ratchet assembly 110 described above, may be incorporated without departing for the novel scope of the present invention.

The present embodiment includes simple means to facilitate the alignment of the interior reel 86 with the exterior case 70 such that replacement of tubing 60 is facilitated. In the placement of tubing 60, within the device of the present invention, tubing reel 86 is aligned with case 70 by rotating an alignment knob 84 to a first indication point 84a, labeled: "REPLACE TUBING". When knob 84 is rotated to first indication point 84a, inlet 87, of reel 86, and tubing guide 78 of case 70 are aligned. A supply of tubing 60 may then be fed into case 70, through inlet 78 and into the hose path 85 of reel 86. Tubing 60 is then threaded through reel hub 94 and out the case tube guide 80. Tube 60 is further connected to the air swivel 82.

Upon the connection of tube 60, in the manner described above, knob 84 is turned to second indication point 84b, labeled "REWIND TUBING" and the desired length of tubing 60 is caused to recoil into case 70. The turning of knob 84 to second indication point 84b allows spring 100 to be released, causing reel 86 to turn in the direction opposite to the previous payout direction (used in removing the used tubing 60 from the device), thus winding the fresh tubing onto reel 86. When replacement of tubing 60 is desired, old tubing 60 is pulled until it is fully extracted, except for that length necessarily engaged in the tubing guide 89. Air swivel 82 may then be removed, and the above procedure may be reversed, allowing the user to attach new tubing 60 and a fresh air swivel 82.

Although an illustrative embodiment of the invention has been shown and described, it is to be understood that various modifications and substitutions may be made by those skilled in the art without departing from the novel spirit and scope of the invention.

What is claimed is:

1. A method of installing therapeutic gas tubing in an therapeutic gas safety and storage reel, including the steps of:

providing a storage case having a tube inlet and a reel alignment opening;

providing a length of tubing;

providing a tube reel, within said case, said reel defining a case alignment opening and comprising a barrel portion defining a tube opening, a hub, and a tube passage between said tube opening and hub, said hub defining the exterior opening of said tube passage, said reel disposed to carry tubing;

aligning said case tube inlet and said barrel tube opening by manipulating said reel and aligning said reel alignment opening with said case alignment opening, respectively on said case and reel;

inserting said tubing into said aligned case tube inlet and said reel tube opening, manipulating said length of tubing through said tube passage to said hub for connection to an external source of therapeutic gas.

2. The method of installing therapeutic gas tubing of claim 1, including the steps of:

paying out substantially all tubing within said case;

aligning said case tube inlet and said barrel tube opening by manipulating said reel and aligning said reel aligning opening and said case alignment opening, respectively on said case and reel;

pulling said tubing from said device;

providing a new length of tubing, and installing said new length of tubing.

3. The method of installing therapeutic gas tubing of claim 2, including the steps of:

providing a spring within said case, attached to said case and reel, such that the payout of tubing causes said spring to be wound tightly; and, providing means to keep said spring wound and means to allow said spring to unwind when desired to rotate said reel causing said tubing to be drawn into said reel and case.

4. A method of installing therapeutic gas tubing in a therapeutic gas storage and safety-reel, including the steps of:

providing a storage case having a tube inlet and a reel alignment opening; providing a length of tubing;

providing a tube reel, within said case, said reel having case alignment means and comprising a barrel portion defining a tube opening, a hub, and a tube passage between said tube opening and hub, said hub defining the exterior opening of said tube passage, said reel disposed to carry tubing;

aligning said case tube inlet and said barrel tube opening by manipulating said reel and aligning said reel alignment means;

inserting said tubing into said aligned case tube inlet and said tube opening manipulating said length of tubing through said tube passage to said hub for connection to an external source of therapeutic gas.

5. The method of installing therapeutic gas tubing of claim 4, including the steps of:

paying out substantially all tubing within said case;

aligning said case tube inlet and said barrel tube opening by manipulating said reel and aligning said reel aligning means;

pulling said tubing from said device;

providing a new length of tubing, and installing said new length of tubing.

6. The method of installing therapeutic gas tubing of claim 5, including the steps of:

providing a spring within said case, attached to said case and reel, such that the payout of tubing causes said spring to be wound; and, providing means to keep said spring wound and means to allow said spring to unwind when desired to rotate said reel causing said tubing to be drawn into said reel and case.

7. A storage and safety reel for therapeutic gas tubing having easy tubing replacement means, comprising:

a reel capable of collecting, holding and paying out tubing for carrying therapeutic gas, such tubing being of the type having a first end and a second end, said reel comprising at least one flange about a generally hollow barrel, said barrel having a surface and a hub, the surface and flange of the reel defining a tube storage area, the surface defining an opening between the tube storage area and hub;

tubing connection means, having a first and second end, said first end of said tubing connection means being releasably attachable to a first end of gas tubing and said second end of said tubing connection means being releasably attachable to a source of therapeutic gas;

said tubing connection means forming a therapeutic gas path when attached to such tubing;

a storage case for housing said reel, said cans defining a first tubing opening, a second tubing opening and cooperative alignment means;

said at least one reel flange defining a cooperative storage case alignment means;

said reel and case being alignable together, by manipulation of said storage case alignment means of said reel and said cooperative alignment mans of said case, such that said second case opening and said opening defined in said surface of said reel are adjacent one another, so that a therapeutic gas path can be removed from said storage and safety reel and a replacement therapeutic gas path installed therefore.

8. The storage and safety reel for therapeutic gas of claim 7, further comprising a spring, attached to said reel and said case, such that the payout of tubing causes said spring to coil.

9. The storage and safety reel for therapeutic gas of claim 8, wherein said spring is a coil spring and the payout of tubing from said reel causes said spring to be coiled.

10. The storage and safety reel for therapeutic gas of claim 8, including a gear and ratchet for locking said spring in a wound position and allowing said spring to unwind when desired.

11. The storage and safety reel for therapeutic gas of claim 10, wherein said gear and ratchet allow said spring to unwind to the extent desired.

12. The storage and safety reel for therapeutic gas of claim 8, including an external spring tensioning socket for independently tensioning said spring.

13. The storage and safety reel for therapeutic gas of claim 7, including an air swivel for connecting air tubing to a source of therapeutic gas.

14. The storage and safety reel of claim 7, wherein said reel and case comprise aseptic surfaces surrounding the therapeutic gas path.

15. A storage and safety reel for therapeutic gas tubing having easy tubing replacement means, comprising:
   a reel capable of collecting, holding and paying out tubing for carrying therapeutic gas, such tubing being of the type having a first end and a second end, said reel comprising at least one flange about a generally hollow barrel, said barrel having a surface and a hub, the surface and flange of the reel defining a tube storage area, the surface defining an opening between the tube storage area and hub;
   tubing connection means, having a first and second end, said first end of said tubing connection means being releasably attachable to a first end of gas tubing and said second end of said tubing connection means being releasably attachable to a source of therapeutic gas;
   an air swivel for connecting said air tubing to a source of therapeutic gas;
   a storage case for housing said reel, said case defining a first tubing opening, a second tubing opening and cooperative alignment means;
   a spring, attached to said reel and said case, such that the payout of tubing causes said spring to coil;
   said tubing connection means forming a therapeutic gas path when attached to such tubing;
   said at least one reel flange defining a cooperative storage case alignment means;
   said reel and case being alignable together, by manipulation of said storage case alignment means of said reel and said cooperative alignment means of said case, such that said second case opening and said opening defined in said surface of said reel are adjacent one another, so that a therapeutic gas path can be removed from said storage and safety reel and a replacement therapeutic gas path installed therefore.

16. The storage and safety reel for therapeutic gas of claim 15, wherein said spring is a coil spring and the payout of tubing from said reel causes said spring to be coiled.

17. The storage and safety reel for therapeutic gas of claim 15, including an external spring tensioning socket for independently tensioning said spring.

18. The storage and safety reel for therapeutic gas of claim 15, including a gear and ratchet for locking said spring in a wound position and allowing said spring to unwind when desired.

19. The storage and safety reel for therapeutic gas of claim 18, wherein said gear and ratchet allow said spring to unwind to the extent desired.

20. A storage and safety reel for therapeutic gas tubing, comprising: a storage case defining a tube opening and a reel alignment opening;
   a reel for storing tubing, said reel defining a case alignment indicator knob, and comprising a barrel having a tube inlet defined therethrough, a hub, and a passageway defined between said tube inlet and said hub;
   said tube opening in said case and said tube inlet in said barrel being alignable, by manipulation of said case alignment indicator knob, such that therapeutic gas tubing can be fed through said case into said reel and subsequently attached to a source of therapeutic gas.

21. The storage and safety reel for therapeutic gas of claim 20, further comprising a spring, attached to said reel and said case, such that the payout of tubing causes said spring to coil.

22. The storage and safety reel for therapeutic gas of claim 21, wherein said spring is a coil spring and the payout of tubing from said reel causes said spring to be coiled.

23. The storage and safety reel for therapeutic gas of claim 21, including a gear and ratchet for locking said spring in a wound position and allowing said spring to unwind when desired.

24. The storage and safety reel for therapeutic gas of claim 23, wherein said gear and ratchet allow said spring to unwind to the extent desired.

25. The storage and safety reel for therapeutic gas of claim 20, including an air swivel for connecting said air tubing to a source of therapeutic gas.

26. A storage and safety reel for therapeutic gas tubing, comprising: a storage case defining a tube;
   a reel for storing tubing, comprising a barrel having a tube inlet defined therethrough, a hub, and a passageway defined between said tube inlet and said hub;
   a reel alignment knob attached to said reel and said storage case;
   an air swivel for connecting said air tubing to a source of therapeutic gas; a spring, attached to said reel and said case, such that the payout of tubing causes said spring to coil;
   said tube opening in said case and said tube inlet in said barrel being alignable, by manipulation of said reel alignment knob, such that therapeutic gas tubing may be fed through said case into said reel and attached to a source of therapeutic gas.

27. The storage and safety reel for therapeutic gas of claim 26, wherein said spring is a coil spring and the payout of tubing from said reel causes said spring to be coiled.

28. The storage and safety reel for therapeutic gas of claim 26, including a gear and ratchet for locking said spring in a wound position and allowing said spring to unwind desired when desired.

29. The storage and safety reel for therapeutic gas of claim 28, wherein said gear and ratchet allow said spring to unwind to the extent desired.

* * * * *